United States Patent [19]

Ikeda et al.

[11] Patent Number: 5,488,169
[45] Date of Patent: Jan. 30, 1996

[54] METHOD OF PRODUCING TETRAKIS(PENTAFLUOROPHENYL)BORATE DERIVATIVES USING PENTAFLUOROPHENYLMAGNESIUM DERIVATIVES

[75] Inventors: Yoshihiko Ikeda, Shinnanyo; Takeo Yamane, Ogori; Eiichi Kaji; Kenji Ishimaru, both of Shinnanyo, all of Japan

[73] Assignee: Tosoh Akzo Corporation, Tokyo, Japan

[21] Appl. No.: 170,762

[22] Filed: Dec. 21, 1993

[30] Foreign Application Priority Data

Dec. 28, 1992  [JP]  Japan .................................. 4-361480
Dec. 1, 1993   [JP]  Japan .................................. 5-329960

[51] Int. Cl.$^6$ .................................. C07F 5/02; C07F 9/02
[52] U.S. Cl. .................................. 568/3; 568/6
[58] Field of Search .................................. 568/6, 3

[56] References Cited

U.S. PATENT DOCUMENTS 2,853,525  9/1958  Wittig et al. .................................. 568/6

OTHER PUBLICATIONS

Zeitschrift fur Naturforschung, vol. 20b, 1965, J. L. W. Pohlmann, et al., "Preparation and Characterization of Group III A Derivatives", pp. 5–11.

Journal of Organometallic Chemistry, vol. 2, 1964, A. G. Massey, et al., "Perfluorophenyl Derivatives of the Elements. I. Tris(Pentafluorophenyl)Boron", pp. 245–250.

March, "Adv. Org. Chem." 2nd Ed (1977) pp. 164–165.

Yang et al, J. Am. Chem. Soc. (1991) 113, 3623–3625.

Kobayashi et al., CA Abstract 100:139179s (1970).

Massey et al., CA Abstract 59:8771b (1963).

Harper et al., JOC, vol. 29, 2385–9 (1964).

Cohen et al., Adv. Fluorine Chem., 6, pp. 119–121 (1970).

Evans et al., Chem. Comm., 67 (1966).

Evans et al., J. Chem. Soc., (A) (1967) p. 1643.

*Primary Examiner*—Joseph Paul Brust
*Attorney, Agent, or Firm*—Oblon, Spivak, McClelland, Maier, & Neustadt

[57] ABSTRACT

A method of producing tetrakis(pentafluorophenyl)borate derivatives of the formula $[(C_6F_5)_4B]_{2-n}MgX_n$ wherein n denotes an integer of 0 or 1 and X denotes a halogen atom, using pentafluorophenylmagnesium derivatives of the formula $(C_6F_5)_{2-n}MgX_n$, wherein n denotes an integer of 0 or 1 and X denotes a halogen atom, as a source of the pentafluorophenyl group.

2 Claims, No Drawings

METHOD OF PRODUCING TETRAKIS(PENTAFLUOROPHENYL)BORATE DERIVATIVES USING PENTAFLUOROPHENYLMAGNESIUM DERIVATIVES

BACKGROUND OF THE INVENTION

The present invention relates to a novel production method of tetrakis(pentafluorophenyl)borate derivatives using pentafluorophenylmagnesium derivatives.

The boron derivatives obtainable according to the invention are very important substances as intermediates of cocatalysts for the cationic complex polymerization reaction.

In recent years, scientific literatures or patents on the studies, in which cationic complexes are generated using tetrakis(pentafluorophenyl)borate derivatives and cyclopentadienyl transition metal complexes, so-called metallocene derivatives, and these are used as catalysts for the polymerization reaction, have increased remarkably. For example, there are Macromol. Chem. Rapid Commun., 2, p.p. 663–667 (1991), etc. Conventionally, however, tetrakis(pentafluorophenyl)borate derivatives have been produced through a process using pentafluorophenyllithium derived from bromopentafluorobenzene as the source of pentafluorophenyl group.

Moreover, pentafluorophenyllithium tends to decompose as the temperature increases and further it decomposes explosively when the temperature exceeds −20° C., hence, usually, it is generated at a temperature as very low as −70° C. and used at the same temperature.

For this reason, installations for low temperature were required, posing a significant problem in the aspect of cost and a problem in the aspect of safety on production as well.

On the other hand, even if attempting to produce tetrakis(pentafluorophenyl)borate derivatives by the same method as the production method of sodium tetraphenylborate described in Experimental Chemistry Series, Vol. 12, "Organometallic Chemistry", p. 307 (published on Mar. 20, 1976, etitor: Corporation Japan Chemical Society, publisher: Maruzen Co., Ltd.), they could not be produced in good yield.

In view of said situation, the inventors investigated extensively on such a production method that pentafluorophenylmagnesium derivatives are used as the source of pentafluorophenyl group on the production of tetrakis(pentafluorophenyl)borate derivatives and very low temperature is unnecessary to be used, leading to the invention.

SUMMARY OF THE INVENTION

The gist of the invention lies in a production method of tetrakis(pentafluorophenyl)borate derivatives characterized by using pentafluorophenylmagnesium derivatives represented by a following formula [IV]

$$(C_6F_5)_{2-n}MgX_n \quad [IV]$$

(wherein n denotes an integer of 0 or 1 and X denotes a halogen atom) as a source of pentafluorophenyl group.

DETAILED DESCRIPTION OF THE INVENTION

In following, the invention will be illustrated concretely.

The concrete method of production will be described below in sequence. In a chain ether type solvent or a mixed solvent of a chain ether type solvent with a hydrocarbon type solvent, 1 equivalent of boron compound represented by a formula [I]

$$BX_3 \quad [I]$$

[wherein X denotes a halogen atom, a substituent represented by a following general formula [II]

$$OR \quad [II]$$

(wherein R denotes a hydrocarbon group with carbon atoms of 1 to 10, and said hydrocarbon group may contain functional groups having no influence on the reaction), or a substituent represented by a following general formula [III]

$$NR'R'' \quad [III]$$

wherein R' and R'' are the same or different and denote a hydrogen atom, a hydrocarbon group of 1 to 20 carbon atoms or a hydrocarbon group of 1 to 20 carbon atoms containing functional groups having no influence on the reaction, or where R' and R'' are linked to one another to form a ring, and wherein said boron compound may form a 1:1 complex with an ether type solvent, is mixed with 3.7 equivalents or more of pentafluorophenylmagnesium derivatives represented by the said formula [IV] within a range from −40° to 250° C. and reacted for 1 hour or longer within a range from 50° to 200° C. to produce tetrakis (pentafluorophenyl)borate derivatives represented by a formula [V]

$$(C_6F_5)_4B_{2-n}MgX_n \quad [V]$$

(wherein n denotes an integer of 0 or 1 and X denotes a halogen atom).

The chain ether type solvents referred to so here indicate ethers having two saturated hydrocarbon groups such as diethyl ether, dipropyl ether, diisopropyl ether, dibutyl ether, diisobutyl ether, dipentyl ether and diisopentyl ether, and the hydrocarbon type solvents indicate aliphatic and aromatic hydrocarbon type solvents with a boiling point of 50° C. or higher.

The use level of pentafluorophenylmagnesium derivatives is 4 equivalents as a theoretical amount when using boron compounds represented by the formula [I] for reaction. But, in the case of under 3.7 equivalents as shown here, a decrease in the yield of tetrakis (pentafluorophenyl)borate derivatives is remarkable, hence use of 3.7 equivalents or more is desirable.

Moreover, when conducting the reaction to produce tetrakis (pentafluorophenyl)borate derivatives represented by the formula [V] by using tris(pentafluorophenyl)borane represented by a formula [VI]

$$(C_6F_5)_3B \quad [VI]$$

or 1:1 complex of tris (pentafluorophenyl)borane with ether type solvent as a boron compound and reacting this with pentafluorophenylmagnesium derivatives represented by the formula [IV], the theoretical amount is 1 equivalent. But, in the case of the use level of tris(pentafluorophenyl)borane represented by the formula [VI] being under 0.7 equivalents, a decrease in the yield of tetrakis(pentafluorophenyl)borate derivatives is remarkable, hence a use of 0.7 equivalents or more is desirable.

As for the mixing temperature of pentafluorophenylmagnesium derivatives with boron compound, since the crystallization sometimes takes place at a temperature lower than −40° C. depending on the kind of pentafluorophenylmagnesium derivatives, a temperature higher than this is desirable, and, since the decomposition of pentafluorophenylmagnesium derivatives takes place at a temperature higher than 250° C., a temperature lower than this is desirable.

Moreover, if the reaction temperature is lower than 50° C., then the progression of reaction is very slow, and, if it is higher than 200° C., then tetrakis(pentafluorophenyl)borate derivatives produced decompose, hence reacting at 50° to 200° C. is desirable.

In accordance with the invention, the effect of the invention is tremendous in the point that a method of producing tetrakis(pentafluorophenyl)borate derivatives being very important substances as the intermediates of cocatalysts for the cationic complex polymerization reaction can be provided in high yield through one process from pentafluorophenylmagnesium derivatives without using pentafluorophenyllithium requiring a reaction at low temperature of −70° C.

In following, the invention will be illustrated in more detail using the examples, but the invention is subject to no restrictions by the following examples so long as it does not exceed the gist.

EXAMPLE 1

In a 200 ml three-neck flask sufficiently replaced with nitrogen, a 18.5 wt. % diethyl ether solution (60.2 g, 41.2 mmol) of pentafluorophenylmagnesium bromide was mixed with boron trifluoride-diethyl ether complex (1.37 g, 9.65 mmol) and toluene 43.4 g, 50 ml) at 25° to 30° C. After the reaction mixture was heated to 85° C. and stirred for 3 hours, the reaction solution was determined quantitatively by means of $^{19}F$ NMR using pentafluorotoluene as an internal standard material to find the yield of tetrakis(pentafluorophenyl)borate derivatives being 100%.

EXAMPLE 2

In a 200 ml three-neck flask sufficiently replaced with nitrogen, a 18.5 wt. % diethyl ether solution (60.2 g, 41.2 mmol) of pentafluorophenylmagnesium bromide was mixed with boron trifluoride-diethyl ether complex (1.39 g, 9.79 mmol) and isopropyl ether (21.8 g, 30 ml) at 25° to 30° C. After the reaction mixture was heated to 69° C. and stirred for 2 hours, the reaction solution was determined quantitatively by means of $^{19}F$ NMR using pentafluorotoluene as an internal standard to find the yield of tetrakis(pentafluorophenyl)borate derivatives being 93.9%.

EXAMPLE 3

In a 200 ml three-neck flask sufficiently replaced with nitrogen, a 18.5 wt. % diethyl ether solution (54.2 g, 37.1 mmol) of pentafluorophenylmagnesium bromide was mixed with boron trifluoride-diethyl ether complex (1.25 g, 8.8 mmol) and dibutyl ether (22.9 g, 30 ml) at 25° to 30° C. After the reaction mixture was heated to 130° C. and stirred for 2 hours, the reaction solution was determined quantitatively by means of $^{19}F$ NMR using pentafluorotoluene as an internal standard to find the yield of tetrakis(pentafluorophenyl)borate derivatives being 93.6%.

EXAMPLE 4

In a 500 ml three-neck flask sufficiently replaced with nitrogen, a 18.5 wt. % diethyl ether solution (131.65 g, 90.1 mmol) of pentafluorophenylmagnesium bromide was mixed with boron trifluoride-diethyl ether complex (3.05 g, 21.5 mmol) and xylene (86.8 g, 100 ml) at 25° to 30° C. After the reaction mixture was heated to 120° C. and stirred for 2 hours, the reaction solution was determined quantitatively by means of $^{19}F$ NMR using pentafluorotoluene as an internal standard to find the yield of tetrakis(pentafluorophenyl)borate derivatives being 96.9%.

EXAMPLE 5

In a 200 ml three-neck flask sufficiently replaced with nitrogen, a 18.5 wt. % diethyl ether solution (60.2 g, 41.2 mmol) of pentafluorophenylmagnesium bromide was mixed with boron trifluoride-diethyl ether complex (1.37 g, 9.65 mmol) and hexane (33.0 g, 50 ml) at 25° to 30° C. After the reaction mixture was heated to 50° C. and stirred for 2 hours, the reaction solution was determined quantitatively by means of $^{19}F$ NMR using pentafluorotoluene as an internal standard to find the yield of tetrakis(pentafluorophenyl)borate derivatives being 78.7%.

EXAMPLE 6

In a 200 ml three-neck flask sufficiently replaced with nitrogen, a 18.5 wt. % diethyl ether solution (60.2 g, 41.2 mmol) of pentafluorophenylmagnesium bromide was mixed with boron trifluoride-diethyl ether complex (1.39 g, 9.79 mmol) and cyclohexane (39.0 g, 50 ml) at 25° to 30° C. After the reaction mixture was heated to 80° C. and stirred for 3 hours, the reaction solution was determined quantitatively by means of $^{19}F$ NMR using pentalfuorotoluene as an internal standard to find the yield of tetrakis(pentafluorophenyl)borate derivatives being 100%.

EXAMPLE 7

In a 300 ml three-neck flask sufficiently replaced with nitrogen, a 18.5 wt. % diethyl ether solution (60.2 g, 41.2 mmol) of pentafluorophenylmagnesium bromide was mixed with a 20.0 wt. % toluene solution of tris(pentafluorophenyl)borane (104.96 g, 41. mmol) at 25° to 30° C. After the reaction mixture was heated to 85° C. and stirred for 3 hours, the reaction solution was determined quantitatively by means of $^{19}F$ NMR using pentalfuorotoluene as an internal standard to find the yield of tetrakis(pentafluorophenyl)borate derivatives being 99.7%.

EXAMPLE 8

In a 300 ml three-neck flask sufficiently replaced with nitrogen, a 18.5 wt. % diethyl ether solution (60.2 g, 41.2 mmol) of pentafluorophenylmagnesium bromide was mixed with a b1 mol/L hexane solution (41.0 mL, 41.0 mmol) of boron trichloride and toluene (100 mL) at 25° to 30° C. After the reaction mixture was heated to 85° C. and stirred for 3 hours, the reaction solution was determined quantitatively by means of $^{19}F$ NMR using pentalfuorotoluene as an internal standard to find the yield of tetrakis(pentafluorophenyl)borate derivatives being 94.1%.

EXAMPLE 9

In a 300 ml three-neck flask sufficiently replaced with nitrogen, a 18.5 wt. % diethyl ether solution (60.2 g, 41.2 mmol) of pentafluorophenylmagnesium bromide was mixed with trimethylboric acid (4.26 g, 41.0 mmol) and toluene (100 mL) at 25° to 30° C. After the reaction mixture was heated to 85° C. and stirred for 3 hours, the reaction solution was determined quantitatively by means of $^{19}F$ NMR using pentafluorotoluene as an internal standard to find the yield of tetrakis(pentafluorophenyl)borate derivatives being 91.2%.

COMPARATIVE EXAMPLE

Into a 200 ml three-neck flask sufficiently replaced with nitrogen, a tetrahydrofuran solution (55.9 g, 41.2 mmol) of pentafluorophenylmagnesium bromide was charged and mixed with boron trifluoride-diethyl ether complex (1.39 g, 9.79 mmol) at 25° to 30° C. After the reaction mixture was stirred for 12 hours at 25° C., the reaction solution was determined quantitatively by means of $^{19}F$ NMR using pentalfuorotoluene as an internal standard to find the yield of tetrakis(pentafluorophenyl)borate derivatives being about 50%.

What is claimed is:

1. A process for producing a tetrakis(pentafluorophenyl)borate compound of the formula V $$[(C_6F_5)_4B]_{2-n}MgX_n \qquad V$$

comprising; mixing in a mixture of diethylether and other chain ether solvent having a boiling point of 50° C. or higher, or in a mixture of diethylether and a hydrocarbon solvent having a boiling point of 50° C. or higher, one equivalent weight of a boron compound of the formula I $$BX_3 \qquad I$$

wherein X denotes a moiety selected from the group consisting of a halogen atom, a substituent represented by the formula II $$OR \qquad II$$

wherein R denotes a hydrocarbon group of 1 to 10 carbon atoms, a hydrocarbon group of 1 to 10 carbon atoms containing functional groups having no influence on the reaction, or a substituent represented by the formula III $$NR'R'' \qquad III$$

wherein R' and R" are the same or different and may be a hydrogen atom, a hydrocarbon group of 1 to 20 hydrocarbons or a hydrocarbon group of 1 to 20 hydrocarbons having a functional group having no influence on the reaction, or R' and R" are linked to one another to form a ring structure, said boron compound being either in the form of a 1:1 complex with an ether type solvent or in non-complexed form;

with 3.7 equivalents or more of a pentafluorophenylmagnesium compound of the formula IV $$(C_6F_5)_{2-n}MgX_n \qquad IV$$

wherein n denotes an integer of 0 or 1 and X denotes a halogen atom; and reacting said mixture at a temperature in the range of 69° to 200° C.

2. A process of producing a tetrakis(pentafluorophenyl)borate compound of the formula V $$[(C_6F_5)_4B]_{2-n}MgX_n \qquad V$$

wherein n denotes an integer of 0 or 1 and X denotes a halogen atom, comprising mixing one equivalent of tris(pentafluorophenyl)borane of the formula VI $$(C_6F_5)_3B \qquad VI$$

or a 1:1 complex of said tris(pentafluorophenyl)borane with ether type solvent, with 0.7 equivalents or more of pentafluorophenyl magnesium compound of the formula IV $$(C_6F_5)_{2-n}MgXn \qquad IV$$

wherein n denotes an integer of 0 or 1 and X denotes a halogen atom, in a mixture of diethylether and other chain ether solvent having a boiling point of 50° C. or higher, or a mixture of diethylether and a hydrocarbon solvent having a boiling point of 50° C. or higher, and reacting said mixture at a temperature in the range 69° C. to 200° C.

* * * * *